United States Patent [19]

Prezmeczky et al.

[11] Patent Number: 5,571,186

[45] Date of Patent: Nov. 5, 1996

[54] PHARMACEUTICAL BONE GROWTH-PROMOTING COMPOSITION AND PROCESS

[75] Inventors: Laszlo Prezmeczky, Basel, Switzerland; Gusztav Klenk, Budapest, Hungary; Erzsebet Englovszky, Vac, Hungary; Tibor Horvath, Budapest, Hungary; Laszlo Miszkiewicz, Budapest, Hungary; Gabor Szekacs, Budapest, Hungary; Ferenc Levai, Budapest, Hungary; Magdolna Vitanyi nee Morvai, Budapest, Hungary

[73] Assignee: Chinoin Gyogyszer es Vegyeszeti Termekek Gyara Rt., Budapest, Hungary

[21] Appl. No.: 282,753

[22] Filed: Jul. 29, 1994

[30] Foreign Application Priority Data

Aug. 2, 1993 [HU] Hungary ................................ 2230/93

[51] Int. Cl.⁶ ........................................ A61F 2/28
[52] U.S. Cl. .............................. 623/16; 433/201.1
[58] Field of Search ........................ 623/16; 433/201.1

[56] References Cited

U.S. PATENT DOCUMENTS

| | | | |
|---|---|---|---|
| 3,949,085 | 4/1976 | Feuer et al. | 514/455 |
| 5,110,720 | 5/1992 | Csányi et al. | 433/215 |
| 5,124,325 | 6/1992 | Kojima et al. | 514/224.2 |
| 5,164,187 | 11/1992 | Constantz et al. | 623/16 |

*Primary Examiner*—Paul B. Prebilic
*Attorney, Agent, or Firm*—Herbert Dubno; Jonathan Myers

[57] ABSTRACT

The invention relates to a combination useful for the substitution of bone defects having pathologically developed or being artificially established as well as compositions containing these combinations. The combinations of the invention preferably contain in a weight ratio of 1:9 to 9:1, most preferably 1:1 porous hydroxylapatite and/or tricalcium phosphate in relation to 7-isopropoxyisoflavone.

8 Claims, No Drawings

PHARMACEUTICAL BONE GROWTH-PROMOTING COMPOSITION AND PROCESS

FIELD OF THE INVENTION

The invention relates to a combination useful for the substitution of bone defects which have pathologically developed or have been artificially established as well as compositions containing these combinations and the process for the preparation thereof.

BACKGROUND OF THE INVENTION

During the last decade, a demand has become more and more pronounced to prevent the loss of teeth or groups of teeth instead of substituting them by removable prostheses.

Because of the disease of the periodontium, the alveolar walls and thereby the mandibles atrophy after removal or loss of a tooth or teeth being close to each other. The solid fixation of a metal implant in atrophied, bone-deficient jaws is problematic.

In the cases of certain diseases, e.g. bone tumors, the bone defect is artificially established by removing the tumor tissue or by a bone fracture.

It is known that porous hydroxylapatite (e.g. CEROS$^R$ 80) or tricalcium phosphate (e.g. CEROS$^R$ 82), respectively are useful bone-substitutive materials in dentistry and maxillary surgery. The drawback of this method consists in that after filling the bone-defective region with a porous hydroxylapatite or tricalcium phosphate by suitable techniques, an amount of new bone providing a safe implantation bed has formed only after 20 months.

OBJECT OF THE INVENTION

Thus, the object of this invention is to develop a combination, which is useful: to substitute artificially established bone defects [e.g. oral (dental) surgery, removal of bone tumors, bone fractures or the like]; to accelerate the regenerative process of bone defect-substitution carried out with hydroxylapatite or tricalcium phosphate known in the art; and/or to achieve a new bone adapted to the demand of bone hardness locally suitable.

It is known that orally administered 7-isopropoxyisoflavone (generic name: IPRIFLAVONE) can be used for the treatment of osteoporosis.

Thus, the present invention relates to a combination useful for substituting bone defects having pathologically developed or being artificially established, which comprises 0 to 99.9% by weight of porous hydroxylapatite and/or tricalcium phosphate and 0.001 to 100% by weight of 7-isopropoxyisoflavone, optionally in the form of discrete granules. The combination according to the invention contains in a weight ratio of 1:9 to 9:1 hydroxylapatite and/or tricalcium phosphate related to 7-isopropoxyisoflavone.

Optionally, the combination according to the invention contains the active ingredients as discrete (physically separate) granules, where the suitable weight ratio is adjusted by varying the amounts of the different granules.

If the composition contains the active ingredients according to the invention together, the composition can preferably be prepared by applying the required amount of 7-isopropoxyisoflavone onto the surface of the porous hydroxylapatite or tricalcium phosphate in a manner known per se (e.g. by wet granulation).

When 7-isopropoxyisoflavone is used in the form of discrete granules, these granules may contain, if desired, also auxiliaries (additives). Useful additives are e.g. polyvinylpyrrolidone, Avicel, Aerosil, methylcellulose, (hydroxypropyl)cellulose, (hydroxymethyl)propylcellulose, starch, mannitol or the like. For the substitution of bone defects, the bone-deficient region is filled by applying suitable surgical techniques with a combination containing porous hydroxylapatite and/or tricalcium phosphate as well as 7-isopropoxyisoflavone, optionally in the form of discrete granules wetted by blood, serum or plasma-substitutes.

The locally suitable bone hardness can be achieved by varying the weight ratio or the particle size of hydroxylapatite and/or tricalcium phosphate used in relation to 7-isopropoxyisoflavone.

In dentistry or in surgery of the jaws, respectively, it is preferred to use a combination, wherein the weight ratio of hydroxylapatite and/or tricalcium phosphate related to 7-isopropoxyisoflavone is 1:1 and the particle size of hydroxylapatite and/or tricalcium phosphate is 0.5 to 0.8 mm.

The combination according to the invention can be used for the substitution of the following bone defects.
In stomatology:
- to fill the dental alveolus remaining after removal of a tooth or teeth, thereby preventing the atrophy of the walls of the dental alveolus;
- to rebuild toothless, severely atrophic dental alveoli for rehabilitation of the set of teeth by using prosthesis or implantation;

In other bone-deficient diseases:
- to substitute bone defects occurring as a consequence of pathologic, inflammatory, tumor diseases or fractures and the like.

During the use of the combination according to the invention it is advantageous to administer 7-isopropoxyisoflavone p.o. as well.

The combination according to the invention and the results achieved by the use thereof, respectively are illustrated by the following non-limiting Example.

EXAMPLE 1

Investigation of the direct mechanism of action on the bone of hydroxylapatite (HA) and ipriflavone (IP)

This experiment was carried out on female Beagle dogs weighing 9 to 15 kg each in the following arrangement of groups.

| Groups of dogs | Ratio of HA:IP |
|---|---|
| I. | 1:1 |
| II. | 6:4 |
| III. | 9:1 |
| IV. | 8:2 |
| V. | IP alone |
| VI. | HA alone |
| VII. | empty bone cavities |

All groups consisted of 4 dogs each. Thus, a total of 28 dogs was operated on and evaluated later.
Description of the surgical intervention After a first incision made on the subjugular mucous membrane of the teeth of proper appropriate size, the bone cavities were established by entering the vestibular bone surface on the right side of the lower jaw-bone of the dogs at the site of the roots of the 4th bicuspid by amputating both roots of this tooth and closing the root-canal of the amputation root-stump by a retrograde root filling well established in human dentistry.

Dimensions of the bone cavities in all dogs were:

about 20 mm in length;

about 8 mm in width;

about 5 mm in depth.

The inlet orifice of the bone cavity was shaped to an elliptic form. Hydroxylapatite and ipriflavone mixed together in a ratio corresponding to the respective group were introduced in the form of discrete granules in such a way that the amount of material soaked by blood reached the bone surface level. The wound of the mucous membrane was tightly closed by a suture of 11 knots on average.

On the 25th day, bone tissue was taken out from all of the 28 dogs for histological examination, in some cases together with the above-lying soft tissues by using the commonly employed method of biopsy sample taking. The following results were obtained:

1. Up to a ratio of 1:1, the higher the amount of ipriflavone was in the ratio of the two substances, the more significant were both the quality and quantity of the newly developed bone. The bone was more compact and its color became more and more similar to that of the nearly intact native bone (it became more and more pale yellow) and the soft, vascularized interstitial elements (showing a reddish-brown color) in the bone structure gradually decreased. From the point of view of ossification, the material obtained by 1:1 weight ratio gave the best results.

2. The regions being in various phases of maturation and the borderlines thereof, were very well discernible on the biopsy bone cylindre.

3. No hydroxylapatite or ipriflavone granules were observed on the bone surfaces recovered or in the depth as well as on the surface of the biopsy cylindre.

4. In the bone cavities containing ipriflavone alone, the newly formed bone was relatively hard and uniform but not to the same degree as the one obtained with combinations of hydroxylapatite and ipriflavone. There were more loose tissue regions among the separate ossifying islets.

5. The consistency of tissues formed in the bone cavity and the connection thereof to the surrounding bone can be characterized as a function of the ratio used as follows.

| Consistency of the tissue | Connection to the surrounding bone | HA:IP ratio |
| --- | --- | --- |
| Compact new bone | Rounded angles; no sharp borderline between the old and new bone | 1:1 |
| Loose new bone | Sharp angles with a well-pronounced borderline | 9:1 |
| Loose new bone with many soft, vascularized tissues | Sharp angles | 1:0 |
| Invaginations of soft parts | Blunted bone borders | — |

It has unambiguously been proven by the above data that the combination according to the invention accelerated bone formation in comparision to the controls.

We claim:

1. A bone growth-promoting composition for rehabilitating a pathologically developed or artificially established bone defect which consists essentially of:
   (a) porous hydroxyapatite or tricalcium phosphate; and
   (b) 7-isopropoxy-isoflavone, in a weight ratio of 1:1 to 9:1.

2. The bone growth-promoting composition defined in claim 1 wherein the weight ratio between the porous hydroxyapatite or tricalcium phosphate and the 7-isopropoxy-isoflavone is 1:1.

3. The bone growth-promoting composition defined in claim 1 wherein each of the porous hydroxyapatite or tricalcium phosphate and the 7-isopropoxy-isoflavone is in a form of discrete granules.

4. The bone growth-promoting defined in claim 3 wherein the particle size of each of the porous hydroxyapatite, tricalcium phosphate or 7-isopropoxy-isoflavone granules is 0.5 to 0.8 mm.

5. The bone growth-promoting composition defined in claim 1 wherein the 7-isopropoxy-isoflavone is applied on the surface of the porous hydroxyapatite or tricalcium phosphate.

6. The bone growth-promoting composition defined in claim 1 wherein the component of (a) is porous hydroxyapatite.

7. A method of rehabilitating a pathologically developed or artificially established bone defect in a mammalian subject which comprises the step of filling a bone deficient region in said mammalian subject with a therapeutically effective amount of a bone growth-promoting composition which consists essentially of:
   (a) porous hydroxyapatite or tricalcium phosphate; and
   (b) 7-isopropoxy-isoflavone, in a weight ratio of 1:1 to 9:1.

8. A process for the preparation of a bone growth-promoting composition for rehabilitating a pathologically developed or artificially established bone defect which consists essentially of:
   (a) porous hydroxyapatite or tricalcium phosphate; and
   (b) 7-isopropoxy-isoflavone, in a weight ratio of 1:1 to 9:1 wherein the 7-isopropoxy-isoflavone is coated on the surface of said porous hydroxy-apatite or tricalcium phosphate, said process comprising the step of:
   applying the 7-isopropoxy-isoflavone onto the surface of the porous hydroxy-apatite or tricalcium phosphate.

* * * * *